United States Patent
Nimgaard (10) Patent No.: US 9,044,266 B2
(45) Date of Patent: Jun. 2, 2015

(54) IMPLANT DEPLOYMENT DEVICE (75) Inventor: Lars S. Nimgaard, Koege (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1479 days.

(21) Appl. No.: 12/284,229

(22) Filed: Sep. 19, 2008

(65) Prior Publication Data

US 2009/0088771 A1   Apr. 2, 2009

Related U.S. Application Data (60) Provisional application No. 60/994,401, filed on Sep. 19, 2007.

(51) Int. Cl.
*A61F 2/06* (2013.01)
*A61B 17/34* (2006.01)
*A61F 2/962* (2013.01)
*A61F 2/95* (2013.01)

(52) U.S. Cl.
CPC .............. *A61B 17/3468* (2013.01); *A61F 2/962* (2013.01); *A61F 2/95* (2013.01)

(58) Field of Classification Search
CPC ........ A61F 2/95; A61F 2/962; A61B 17/3468
USPC .................... 23/1.11, 1.12, 1.23; 606/108; 604/165.01, 165.04; 623/1.11, 1.12, 623/1.23
See application file for complete search history.

(56) References Cited

U.S. PATENT DOCUMENTS

| | | | |
|---|---|---|---|
| 4,682,981 A | | 7/1987 | Suzuki et al. |
| 5,700,269 A | * | 12/1997 | Pinchuk et al. ............... 606/108 |
| 6,589,251 B2 | | 7/2003 | Yee et al. |
| 6,589,262 B1 | * | 7/2003 | Honebrink et al. ........... 606/191 |
| 7,022,133 B2 | * | 4/2006 | Yee et al. ...................... 623/1.11 |
| 2004/0193243 A1 | * | 9/2004 | Mangiardi et al. ........... 623/1.11 |
| 2005/0059990 A1 | * | 3/2005 | Ayala et al. ................... 606/192 |
| 2005/0113902 A1 | * | 5/2005 | Geiser et al. ................. 623/1.11 |
| 2008/0255542 A1 | | 10/2008 | Nimgaard et al. |

* cited by examiner

*Primary Examiner* — Katherine Dowe
(74) *Attorney, Agent, or Firm* — Richard J. Godlewski; Taiwoods Lin (57) ABSTRACT

An implant deployment device (10) includes a pusher member (30), inner catheter (24), dilator tip (20) upon which an implant (18) is supported during deployment into a lumen of a patient. A sheath (32) substantially surrounds the pusher member (30), the inner catheter (24), the dilator tip (20), covering the implant (18) and containing the implant (18) therewithin. The pusher member (30), inner catheter (24), dilator tip (20) has at least one longitudinal groove formed in its outer surface. This engages with at least one tooth (112) formed in an inner surface of the sheath (32) or an inner surface of a component of the device that is attached to the sheath (32), such as a clamping collar (90) or a locking unit (100). The tooth (112) engages with a longitudinal groove (80) and is able to move along the groove (80) in a longitudinal direction. The engagement of the tooth (112) within the groove (80), however, prevents relative rotation between the sheath (32) and the pusher member (30), inner catheter (24), dilator tip (20). Twisting of an implant (18) supported on the inner catheter (24) is thus avoided.

19 Claims, 6 Drawing Sheets

IMPLANT DEPLOYMENT DEVICE

CROSS-REFERENCE TO RELATED APPLICATIONS

This application claims priority of provisional application Ser. No. 60/994,401, filed Sep. 19, 2007.

TECHNICAL FIELD

The present invention relates to an implant deployment device. In particular, the implant deployment device is designed to prevent or limit relative rotation between an implant support element and a surrounding sheath.

BACKGROUND OF THE INVENTION

Implant deployment devices for introducing intraluminally a stent, stent graft or other implant or prosthesis are typically provided with an outer sheath within which there is provided an implant support element or deployment mechanism such as an inner catheter or cannula which may include a pusher rod and dilator. The sheath has the function of containing various components of the implant deployment device, and in particular the implant, therewithin during the intraluminal introduction procedure. This flexes and twists as it passes through the various lumens of the patient, until it reaches the location at which the implant being carried needs to be positioned. The sheath is typically of a construction that is flexible so it can be passed relatively easily through lumens of a patient and yet be able to withstand rotational torque. Rotation is important during the implant placement process. For example, the implant may need to be rotated at the implantation site to ensure that it is placed in the correct orientation. For this purpose, the sheath is of a length that extends, normally, to a dilator tip at the distal end of the implant deployment device and also to outside the insertion site in the patient and, for example, to outside the femoral artery. This end is typically termed the proximal end. This proximal end of the sheath typically has fitted integral therewith a plurality of manipulation elements for controlling the introduction of the sheath into the patient, and the release of the implant, as well as for supplying various fluids during the medical procedure, such as saline solution or necessary medicaments.

Typically, the implant is located at the end of a pusher rod, which is itself flexible, and which extends from the proximal end to the distal end of the implant deployment device and within the sheath.

A problem can occur when using prior art implant deployment devices, and, in particular, when it is necessary to twist the implant deployment device in order to rotate the distal end of the implant deployment device to ensure correct orientation of that end of the device, and, in the case of deployment of a prosthesis or implant, correct orientation of the implant in the patient. With prior art devices, when the surgeon attempts to rotate the proximal end of the deployment device, once the inner catheter has been unlocked from the sheath, that is, when the surgeon rotates the end external to the patient, relative rotation between the pusher member and the sheath and therefore incorrect rotation of the distal end of the deployment device can occur. This can result in incorrect placement of an implant and in some cases can also lead to twisting of the implant because of the torque generated between the sheath and the pusher member at the distal end of the device.

U.S. Pat. No. 4,682,981 discloses a medical device for introducing a catheter into a blood vessel of a patient. A locking device has grooves and ribs provided in a main body of the medical device and in a dilator portion of the medical device. The ribs and grooves interengage and thus prevent movement between the main body and the dilator portion. The ribs and grooves thus act as a locking device, which prevents both rotational and axial movement between the main body and the dilator. With this device it would not be possible to manipulate the implant support element in the axial direction (for example, to move a pusher member distally) whilst the locking device is locked. Once unlocked, both axial and rotational movement are enabled. Therefore, this lock is seen only as an alternative to conventional sheath locking devices, which lock longitudinally and rotationally until released.

U.S. Pat. No. 6,589,251 addresses the problem of rotational movement of the sheath relative to the inner catheter or pusher rod. It discloses a multi-sheath delivery catheter in which telescopically arranged sheaths are respectively attached to a handle. The transverse shapes of the facing surfaces are complementary and non-round in cross-section. For example, they may be square, triangular, oval or D-shaped. Whilst this arrangement prevents relative rotation between the handles, the solution is unsatisfactory for several reasons. A non-round cross-section has increased likelihood of jamming of the telescopic components. Furthermore, they suffer from uneven flexibility in different radial directions, and increased risk of kinking. It is also difficult to make such devices sufficiently small for many medical applications.

SUMMARY OF THE INVENTION

The present invention seeks to provide an improved implant deployment device.

According to a first aspect of the present invention, there is provided an implant deployment device including: an implant support element onto which an implant may be mounted prior to deployment; a sheath assembly including a sheath operable to cover an implant carried on said implant support element until deployment, said sheath being retractable relative to said implant support element, wherein said sheath has an inner surface and said implant support element has an outer surface, wherein said inner surface of said sheath faces said outer surface of said implant support element; said inner and outer surfaces being generally round in transverse cross-section; and at least one co-operating guide and guide follower being provided on said sheath assembly and implant support element for preventing relative rotation of said sheath and implant support element as said sheath is retracted.

This implant deployment device allows a sheath to be retracted from an implant that may be mounted on the implant support element without relative rotation between the sheath and the implant support element. The generally round transverse cross-section allows the size of the component parts to be minimized, ensures that flexibility of the device is even in different radial directions, reduces the risk of jamming between the component parts and reduces the risk of kinking.

The generally round transverse cross-section typically includes a circumference that is at least 70% circular. More preferably the cross-section is 70 to 90% circular, even more preferably the cross-section is 80 to 90% circular.

The guide and guide follower may include a channel and projection. The projection is able to slide along the length of the channel.

In an embodiment, the channel is provided in the outer surface of the implant support element and the projection is provided on an inner surface of the sheath assembly. These may be preferred as they are simple to fabricate.

The channel may have a depth in the range of 10 to 20% of the diameter of the implant support element. This provides an appropriate size of groove without affecting the properties of the implant support element.

Preferably the channel and the projection have substantially the same shape in transverse cross-section. The more similarly matched the indentation and projection are, the less rotation is possible.

The channel may have a substantially V-shaped cross-section and the projection may also have a substantially V-shaped cross-section. The walls of the channel and/or the projection may slope towards one another at an angle in the range of from 45° to 60°, for example. In an alternative embodiment, the channel has a substantially square or rectangular cross-section and the projection has a substantially square or rectangular cross-section.

In an embodiment, at least one guide or guide follower is provided on said sheath assembly as part of an external manipulation unit of said implant deployment device; and at least one guide or guide follower is provided on said sheath assembly at a distal end of said implant deployment device.

The device may include an implant mounted on the implant support element.

According to a second aspect of the present invention, there is provided an implant deployment device including: an implant support element onto which an implant may be mounted prior to deployment; a sheath assembly including a sheath operable to cover an implant carried on said implant support element until deployment, said sheath being retractable relative to said implant support element, wherein said sheath has an inner surface and said implant support element has an outer surface, wherein said inner surface of said sheath faces said outer surface of said implant support element; said inner and outer surfaces being generally round in transverse cross-section, wherein said generally round transverse cross-section is 80 to 90 percent circular; and at least one co-operating channel and projection being provided on said sheath assembly and implant support element, said channel and said projection having substantially a same shape in transverse cross-section, for preventing relative rotation of said sheath and implant support element as said sheath is retracted.

BRIEF DESCRIPTION OF THE DRAWINGS

Embodiments of the present invention are described below, by way of example only, with reference to the accompanying drawings, in which.

DETAILED DESCRIPTION

It is to be understood that the Figures are schematic and do not show the various components in their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practise in or adjacent an external manipulation part of the deployment or treatment apparatus.

On the other hand, when referring to an implant such as a stent or stent graft, the term proximal refers to a location which in use is closest to the patient's heart, in the case of a vascular implant, and the term distal refers to a location furthest from the patient's heart.

Figure 1:
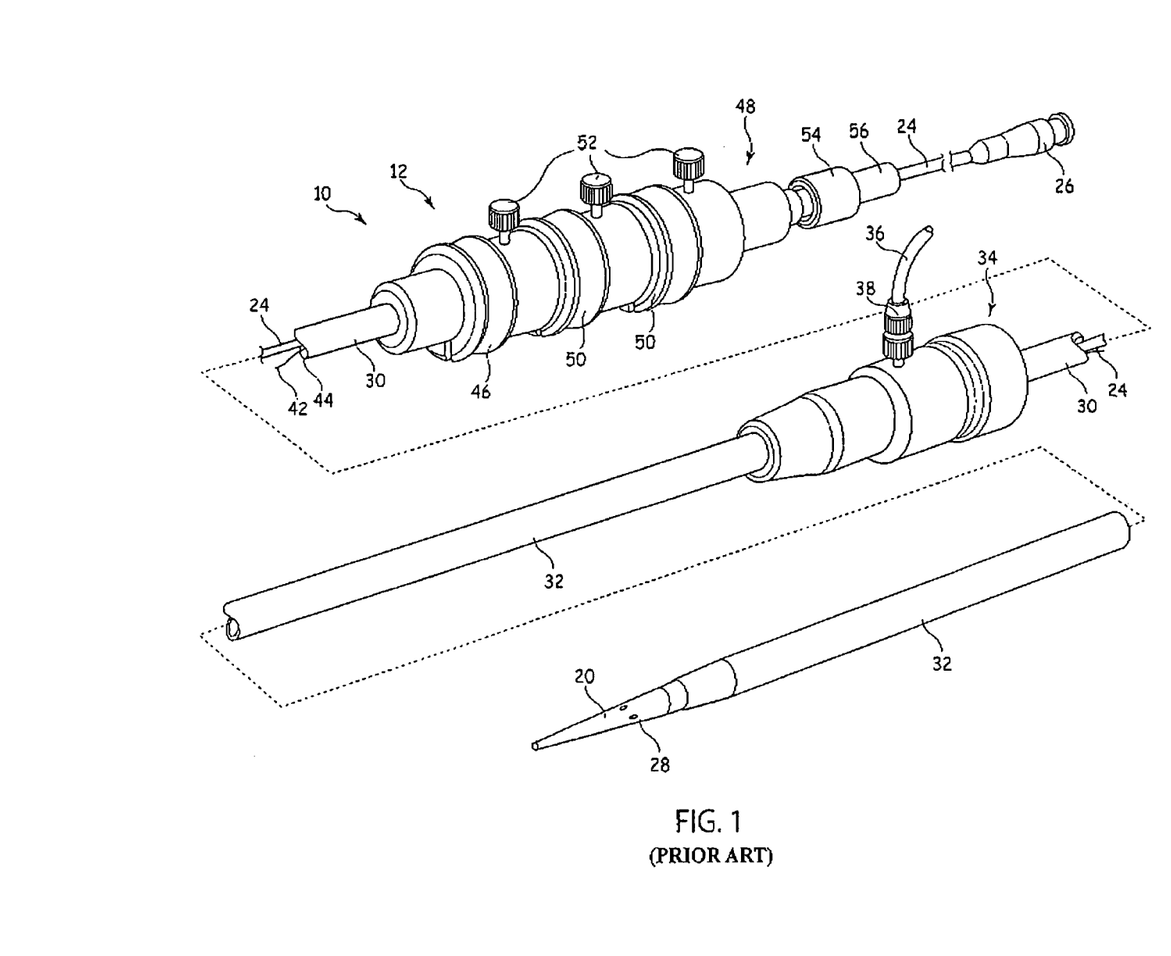
FIGS. 1 and 2 show an example of a known implant deployment device.
Figure 2:
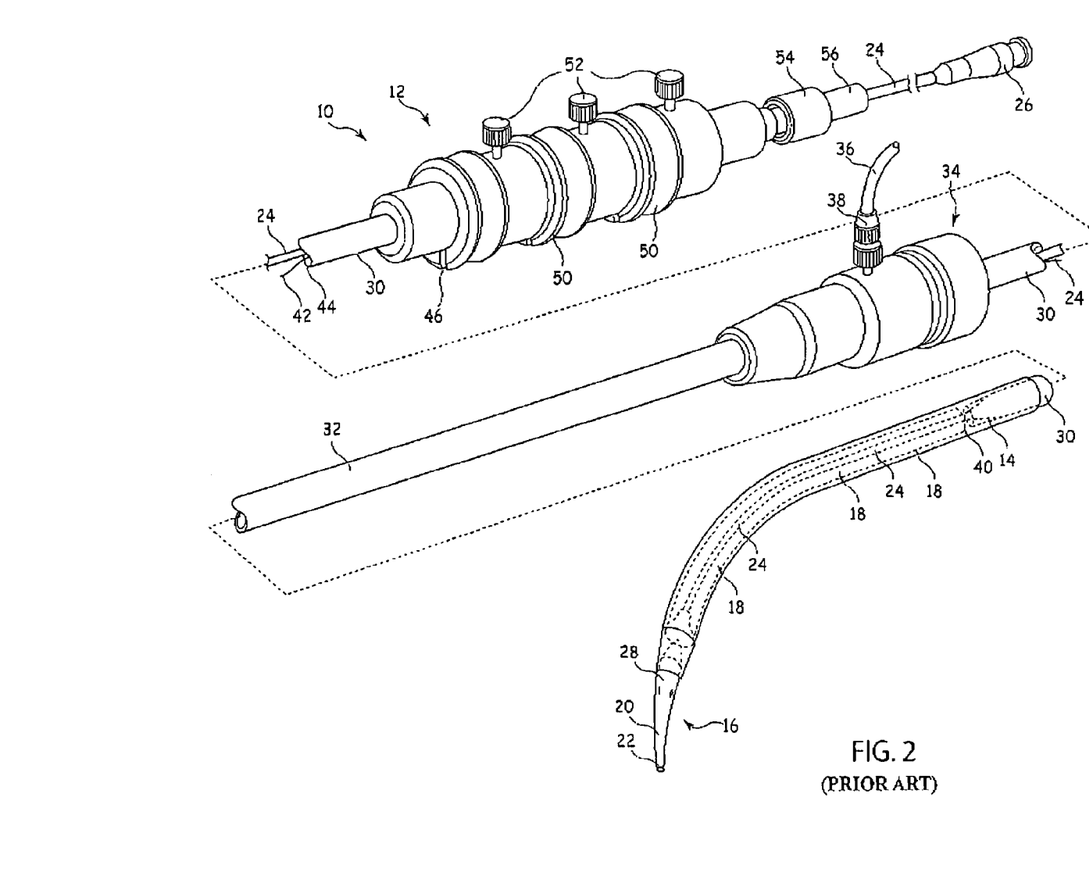

Referring to FIGS. 1 and 2, an implant deployment device 10 includes an external manipulation section 12, a proximal attachment region 14 and a distal attachment region 16. The proximal attachment region 14 and the distal attachment region 16 secure the two ends of the implant 18. During the medical procedure to deploy the implant 18, the proximal and distal attachment regions 14 and 16 will travel through the patient's vasculature, in this example, to a desired deployment site. The external manipulation section 12 at the proximal end of the implant deployment device 10, which is operated by a surgeon to manipulate the introducer, remains outside of the patient throughout the procedure.

The distal attachment region 16 of the implant deployment device 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

An inner catheter or cannula 24, conventionally made from a flexible thin walled metal tube, is fastened to the dilator tip 20. The inner catheter 24 is flexible so that the implant deployment device 10 can be advanced along a relatively tortuous vessel, such as a femoral artery, and so that the distal end of the implant deployment device 10 can be longitudinally and rotationally manipulated. The inner catheter 24 carries a stent 18 or other device to be implanted in the patient. The catheter 24 extends through the implant deployment device 10 to the manipulation section 12, terminating at a connection device 26, in conventional manner.

The connection device 26 is designed to accept a syringe to facilitate the introduction of reagents into the inner catheter 24 and for this purpose is typically provided with a threaded luer lock connection.

Where provided, a pusher sheath or rod 30 (hereinafter referred to as a pusher member), typically made from a plastics material, is mounted coaxial with and radially outside of the inner catheter 24. The pusher member 30 is "thick walled", that is the thickness of its wall is preferably several times greater than that of the guide wire catheter 24. In some instances, the pusher member 30 and the inner catheter 24 are the same component, possibly having different outer diameters at the location at which the stent 18 is to be carried.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by the implant deployment device 10, is retained in a compressed condition by the sheath 32. The sheath 32 extends proximally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The side tube 38 facilitates the introduction of medical fluids between the pusher member 30 and the sheath 32. Saline solution is typically used.

During assembly of the implant deployment device 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher member 30 and retains a distal end 40 of the prosthesis 18 during the procedure. The distal end of the prosthesis 18 may be provided with a loop of material (not shown) through which a distal restraining wire 42 extends. The distal restraining wire also extends through an aperture (not shown in FIGS. 1 and 2) in the proximal attachment section 40 into an annular region 44 between the inner catheter 24 and the pusher member 30. The distal restraining wire 42 extends through the annular space 44 to the manipulation region 12 and exits the annular space 44 at a distal wire release mechanism 46.

A proximal portion of the external manipulation section 12 includes at least one restraining wire actuation section 50 mounted on a body 48, in turn mounted onto the pusher member 30. The inner catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism or mechanisms 50 must be moved before the distal wire release mechanism 46 can be moved, such that the proximal end of the implant, that is the end of the implant which will be upstream in the direction of fluid flow in the patient's vasculature, is released first. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the inner catheter 24. When the vise jaws are engaged, the inner catheter 24 can only move with the body 48 and hence it can only move with the pusher member 30. With the screw cap 56 tightened, the entire assembly can be moved together as one piece.

Once the implant deployment device 10 is in the desired deployment position, the sheath 32 is withdrawn to just distal of the proximal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end of the self-expanding stent however, is still retained at the distal attachment region 16 by means of the restraining wires. Also, the distal end of the stent or stent-graft 18 is still retained within the sheath 32.

Next, the pin vise 54 is released to allow small movements of the inner catheter 24 with respect to the pusher member 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the implant.

When the proximal end of the stent or stent-graft 18 is in place, the proximal restraining wire (not shown) is withdrawn by movement of the proximal wire release mechanism 50. The proximal wire release mechanism 50 and the proximal restraining wire can be completely removed by passing the proximal wire release mechanism 50 over the pin vice 54, the screw cap 56 and the connection unit 26.

Next, the screw cap 56 of the pin vise 54 is loosened, after which the inner catheter 24 can be pushed in a distal direction, that is towards the inside of the patient, so as to move the dilator tip 20 in a distal direction. This fully releases the proximal end of the stent or stent-graft 18, allowing it to expand so as to engage the lumen walls of the artery or vein. From this stage on, the proximal end of the stent or stent-graft 18 cannot be moved again.

Once the proximal end of the stent or stent-graft 18 is anchored, the sheath 32 is withdrawn proximally of the proximal attachment section 14, which withdrawal allows the distal end of the stent or stent-graft 18 to expand. Until this point and in particular until the distal release mechanism 46 is actuated to release the distal restraining wires from the distal end of the stent 18, the distal may still be repositioned as needed.

For some procedures, the sheath 32 may be left in place after expansion of the implant 18. The pusher member 30 and inner catheter 24 may be withdrawn and replaced by a further component, using the sheath 32 as a guide.

Figure 3:
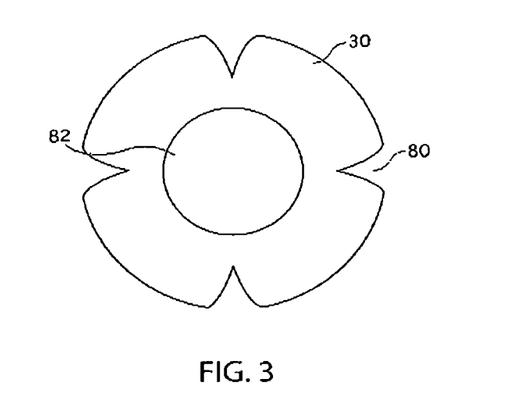
FIG. 3 shows a cross-section of a pusher member of a preferred embodiment.
Figure 4:
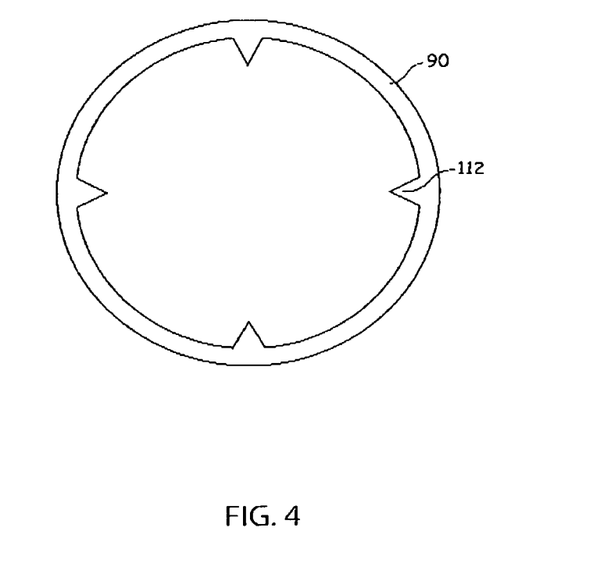
FIG. 4 shows a cross-section of a part of the implant deployment device for engagement with the pusher member of FIG. 3.

Referring to FIGS. 3 and 4, in a preferred embodiment, an implant deployment device 10 includes a pusher member 30. The pusher member 30 (in this example) also functions as a catheter, since a bore 82 runs longitudinally therethrough. An implant 18 such as a stent or stent-graft may be carried at a distal end of the pusher member 30. The pusher member 30 essentially functions as described above with reference to FIGS. 1 and 2 and includes a dilator tip 20 at its distal end.

The pusher member 30 is provided with longitudinal grooves 80 along at least a part of its length equivalent to the expected retraction distance of the outer sheath. In this embodiment, four grooves are provided at approximately 90° intervals. The grooves have a substantially V-shaped cross-section. The walls of the grooves preferably slope at an angle of approximately 45 to 60° and extend to a depth of approximately 20% of the diameter of the pusher member 30.

FIG. 4 shows a guide collar 90, which may form a part of the haemostatic sealing unit 34, pin vise 54 or any other component of the external manipulation unit of the implant deployment device 10 as illustrated in FIGS. 1 and 2. The guide collar 90 is fixed so as to move with the sheath 32 that extends coaxially with the pusher member 30, substantially surrounding the pusher member 30 and any implant 18 supported thereon. The guide collar 90 may also in some embodiments be the sheath 32 itself or a part of the sheath 32 and could easily be created as an extension of the sheath 32 by means of a suitably shaped extrusion dye.

It can be seen from FIG. 4 that the guide collar 90 is provided with four radially inwardly extending teeth 112. These are provided at approximately 90° intervals in order to correspond with the grooves 80 provided in the pusher member 30. When the pusher member 30 resides within the guide collar 90 the teeth 112 sit within and can slide along the grooves 80.

The teeth 112, are sized so that when engaged with the grooves 80, they do not reach the base of the grooves 80. The teeth 112, are thus able to slide within the grooves 80. Furthermore, the teeth 112 extend in the longitudinal direction of the implant deployment device 10 to a lesser extent than the grooves 80.

With reference also to FIGS. 1 and 2, it can be seen that, in use, the location of the teeth 112 within their respective grooves 80 prevents relative rotation between the sheath 32 and the pusher member 30 or inner catheter 24 while the sheath is being retracted. In other words, rotation of the sheath 32 results also in rotation of the pusher member 30 and inner catheter 24 to the same extent. The implant 18 is thus protected from twisting due to the torque generated between the sheath 32 and the pusher member 30 or inner catheter 24. It is nevertheless to be noted that axial movement between the sheath 32 and the pusher member 30 or inner catheter 24 is possible since the teeth 112 are able to move along the longitudinal grooves 80 provided in the pusher member 30. This arrangement, therefore, still enables the sheath 32 to be withdrawn, or the pusher member 30 to be moved distally.

Figure 5:
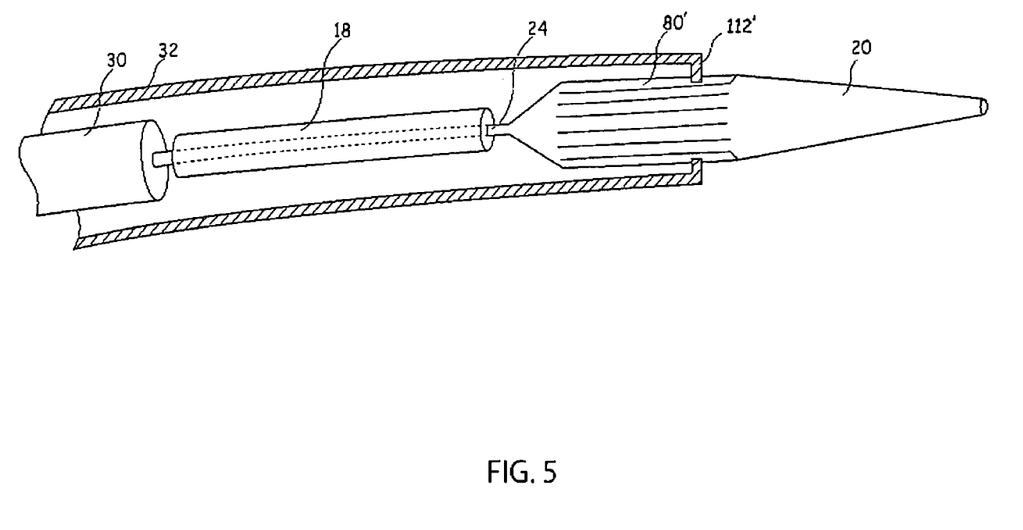
FIG. 5 shows a longitudinal cross-section of the distal part of a preferred implant deployment device.

FIG. 5 shows the distal end of a preferred implant deployment device 10. The pusher member 30 has an implant support part (catheter 24) with an implant 18 carried thereon. Distally of the catheter 24 is a dilator tip 20. The pusher member 30, catheter 24, dilator tip 20 are at least partially surrounded by a sheath 32.

The dilator tip 20 includes a plurality of longitudinal grooves 80' spaced around its circumference. Inwardly extending teeth 112' are provided at the distal end of the sheath 32. Analogously to the situation in FIGS. 3 and 4, the teeth 112' of the sheath 32 interengage with the grooves 80' of the dilator tip 20. The teeth 112' at the distal end of the sheath 32 and the grooves 80' of the dilator also preferably have a substantially V-shaped cross-section.

The structure of FIG. 5 is optional. When it is used, it also prevents rotation of the dilator tip 20 relative to the sheath 32, which can be particularly useful when a deployment device is to be fed through particularly tortuous paths. All features of the teeth 112 and the grooves 80 described above with respect to FIGS. 3 and 4 apply equally to the teeth 112' and the grooves 80' illustrated in FIG. 5.

In a particular embodiment, the subject matter of this application may be used in conjunction with that disclosed in U.S. Ser. No. 60/922,789. The contents of that patent application are hereby incorporated by reference herein.

Figures 6, 7:
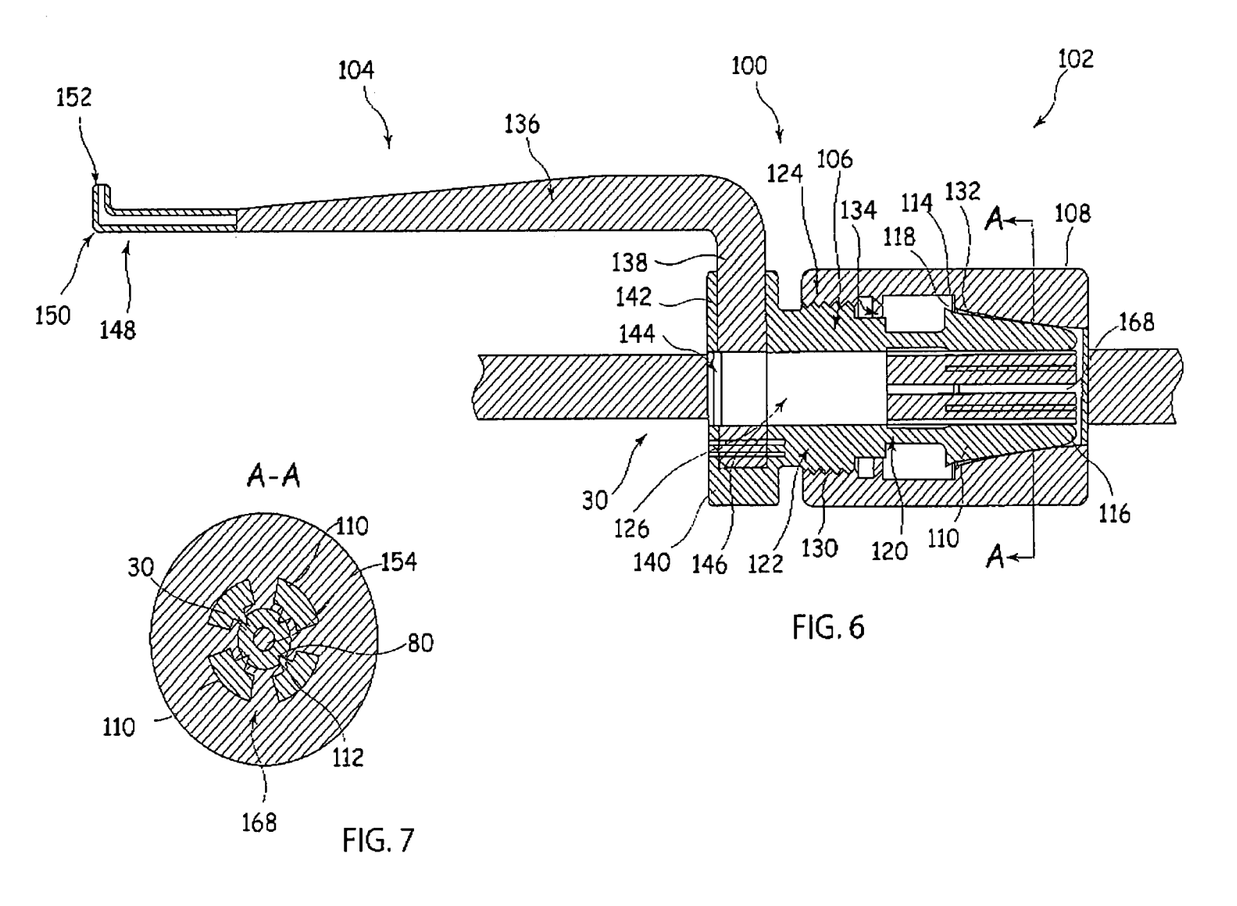
FIG. 6 is a cross-sectional view in side elevation of a locking unit that may be used with the pusher member of FIG. 3.
FIG. 7 is a view of the device of FIG. 6 in cross-section taken along line A-A of FIG. 6.

FIGS. 6 and 7 illustrate a locking device as described in U.S. Ser. No. 60/922,789. FIG. 6 shows a cross-sectional view in side elevation of the preferred embodiment of locking unit 100. This embodiment includes two portions, a first portion 102 which provides a longitudinal locking function and a second portion or arm 104 which provides a radial locking action.

The first portion 102 is formed of an inner gripping member 106 and an outer nut 108. The inner gripping member 106 is provided with a plurality of cantilevered fingers 110, in this embodiment there being four such fingers 110 although other numbers of fingers may be provided. Along an inner surface of each finger 110 and extending along its longitudinal axis, there is provided a tooth 112, which preferably has a triangular shape in transverse cross-section, as shown in particular in FIG. 7.

The outer surface 114 of each cantilevered finger 110 is curved in a convex manner in its longitudinal direction, as well as being curved in its radial direction. These outer surfaces 114 also widen from the ends of each cantilevered finger, as is readily visible in FIG. 6. At the end of the curved section of each surface 114, there is provided an outwardly extending flange or shoulder 118 and beyond that a section 120 of reduced outer diameter. As will be apparent from FIG. 6 in particular, the flange 118 is discontinuous, being located on the cantilevered portions of the fingers 110 and thus split by the gaps 168 between the fingers.

The reduced outer diameter section 120 terminates, in this embodiment, at the ends of the cantilevered fingers 110 and is integral with an annular portion 122. The annular portion 122 is provided with an external screw thread 124.

The cantilevered fingers 110 and the annular portion 122 provide an internal bore 126 for the passage of the pusher member 30 of FIG. 3 therethrough.

The inner gripping member 106 is preferably made of a plastics material, although it could be made of any other material which allows the cantilevered fingers 110 to be resiliently deformable, at least at the zone 120 of reduced outer diameter.

A nut 108 includes at one end an internal threaded section 130 with threads which are matched to the external threads 124 of the inner gripping member 106.

At the other end of the nut 108, there is provided an internal tapering surface 132 which in this embodiment provides a frusto-conical surface tapering away from the internal threaded section 130 and in the same direction as the taper of the outer surfaces 114 of the cantilevered fingers 110. In this embodiment, the surface forming the internal tapering section 132 is substantially straight, such that when the nut 108 is fitted onto the inner gripping member 106, as shown in FIG. 6, there is only partial contact between the inner surface of the tapering section 132 and the outer surfaces 114 of the cantilevered fingers 110. This has the advantage of providing the desired biasing action on the cantilevered fingers 110, as described below, while reducing the surface area contact between the cantilevered fingers 110 and the nut 108, thereby to reduce any friction between these two components. Moreover, this tangential contact of the outer surfaces 114 of the cantilevered fingers 110 and the internal tapering surface 132 maintains a good closing action on the fingers 110 as the nut 108 is tightened.

Between the internal threaded section 130 and the tapering section 132 of the nut 108, there is provided an internally extending annular flange 134 which provides a second shoulder facing and opposite to the outwardly extending annular flange or shoulder 118 of the inner gripping member 106.

The nut 108 is preferably also made of a plastics material and most preferably a material which is substantially rigid. Advantageously, the outer surfaces of the nut 108 are provided with one or more markings to assist a user in rotating the nut 108 in locking and/or unlocking directions.

Referring now to FIG. 7, there is shown a cross-sectional view of the device taken along line A-A of FIG. 6. There can be seen located within the cantilevered fingers 110 the pusher member 30 of FIG. 3, and within that a guide wire 154 of conventional form.

The teeth 112 of the cantilevered fingers 110 engage with the longitudinal grooves 80 provided in the outer surface of the pusher member 30.

When the locking nut 108 of the locking unit 100 is in an unlocked position, the internal tapered surface 132 thereof applies no or substantially no biasing force against the cantilevered fingers 110, allowing them to hold their unbiased open positions. This enables the pusher member 30 to slide freely within the locking unit 100.

The nut 108 can be rotated to its closed position, that is rotated such that it moves towards the left as in the views of FIG. 6 by virtue of the engagement of the threaded elements 124 and 130. This causes a progressively stronger biasing force to be applied to the cantilevered fingers 110 by virtue of the reducing diameter of that part of the tapering section 132 of the nut 108 which applies pressure to the fingers 110. This biasing action causes the fingers 110 to be urged towards the pusher member 30 and eventually for the teeth 112 to dig into the pusher member 30. In practice, as the fingers 110 are pushed inwardly, the gaps 168 between the fingers 110 diminish.

Once the teeth 112 embed into the outer surface of the pusher member 30, they provide a very strong and reliable locking action of the locking unit 100 to the sheath 32. This has the advantage that a strong gripping effect can be achieved without requiring a large surface area contact to be provided between the cantilevered fingers 110 and the outer surface of the pusher 128 or other longitudinal element positioned in the bore 126 inside the inner gripping member 106. Therefore, when locked, the locking unit 100 provides a strong and reliable locking action of the pusher member 30 relative to the sheath 32.

When the locking nut 108 is released, the teeth 112 still reside within the longitudinal grooves 80 of the pusher member 30 without digging into the outer surface thereof. At such a position, longitudinal movement between the pusher member 30 and the locking unit 100 is possible, but rotational movement therebetween (and thus between the pusher member 30 and the sheath 32) is prevented.

In a modification, shorter teeth 112 are provided. When the locking nut 108 is fully released, the teeth 112 no longer project into the longitudinal grooves 80. In such a case, full release of the locking nut 108 allows both longitudinal and rotational movement.

The skilled person would appreciate that many other modifications could be made to the above described embodiment. For example, the grooves in the pusher member 30 and/or dilator tip 20 may be of different form and number to that described above.

Figure 8:
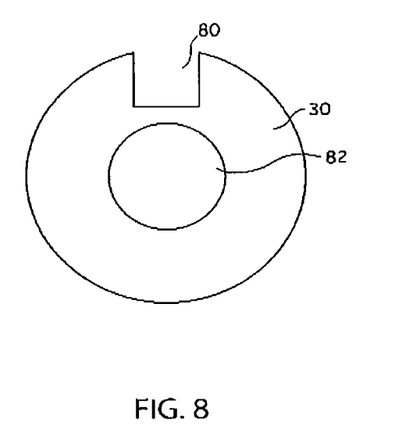
FIG. 8 shows a cross-section of another embodiment of a pusher member.
Figure 9:
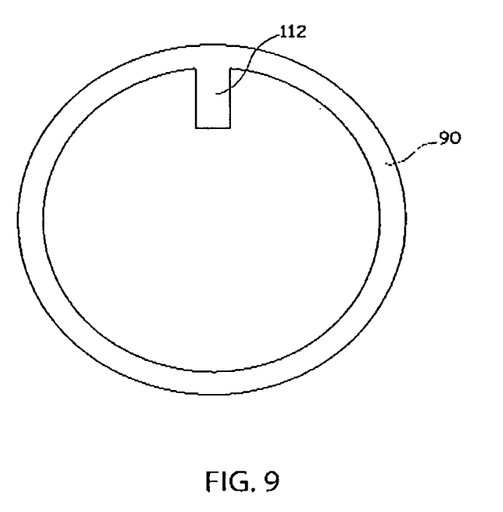
FIG. 9 shows a cross-section of a part of the implant deployment device for engagement with the pusher of FIG. 8.

FIGS. 8 and 9 illustrate an embodiment where only a single longitudinal groove 80 is provided with a corresponding single tooth 112 in the guide collar 90. Whilst FIGS. 8 and 9 illustrate a pusher member 30 and a corresponding guide collar 90, it will be appreciated that the illustrated arrangement is equally applicable to a dilator tip 20 and a tooth 112' on a corresponding sheath 32 (c.f FIG. 5).

Other arrangements may, of course, be envisaged. For example, the pusher member 30 or dilator tip 20 could include longitudinal ribs; corresponding slots could be formed in the guide collar 90 or in a collar at the distal end of the sheath 32. Additionally or alternatively, grooves could be provided in the internal surface of the sheath. Another arrangement may involve grooves in the internal surface of the sheath and teeth on the outer surface of the pusher member or dilator tip.

The teeth 112 may be formed at any suitable part of the implant deployment device 10. Preferably they are at least formed on an inner surface of a part of the outer assembly of the implant deployment device 10. For example, additionally or alternatively to being formed as part of a haemostatic valve assembly, haemostatic sealing unit 34, or locking unit 100, they could be formed as part of a deployment handle or the fluid chambers.

In some cases the arrangement may be such that rotation is possible during part of the sheath withdrawal process. The skilled person would appreciate how the above-described embodiments could be modified to provide such a feature.

The contents of U.S. Ser. No. 60/994,401 from which this application claims priority and of the Abstract accompanying this application are herein incorporated by reference.

What is claimed is:

1. An implant deployment device including:
an implant support element onto which an implant may be mounted prior to deployment;
a dilator tip distal of an implant;
a sheath assembly including a sheath operable to cover an implant mounted on said implant support element and to cover at least part of said dilator tip, said sheath being retractable relative to said implant support element, wherein said sheath has an inner surface and said dilator tip has an outer surface, wherein said inner surface of said sheath faces said outer surface of said dilator tip;
a locking mechanism including at least one co-operating channel and projection being provided on said inner surface of said sheath assembly and on said outer surface of said dilator tip at or near a distal end thereof; and
wherein each of said inner and outer surfaces has a generally round transverse cross section at the location of the locking mechanism, wherein said generally round transverse cross-section includes a circumference that is at least 70 percent circular.

2. The device of claim 1, wherein said generally round transverse cross-section is 70 to 90 percent circular.

3. The device of claim 2, wherein said generally round transverse cross-section is 80 to 90 percent circular.

4. The device of claim 1, wherein said sheath assembly has an inner surface, wherein said channel is provided in said outer surface of said dilator tip and said projection is provided on said inner surface of said sheath assembly.

5. The device of claim 4, wherein said implant support element has a diameter, and wherein said channel has a depth in the range of 10 to 20 percent of said diameter of said implant support element.

6. The device of claim 4, wherein said implant support element has a diameter, and wherein said channel has a depth of approximately 10 percent of said diameter of said implant support element.

7. The device of claim 4, wherein said implant support element has a diameter, and wherein said channel has a depth of approximately 20 percent of said diameter of said implant support element.

8. The device of claim 1, wherein said channel and said projection have substantially a same shape in transverse cross-section.

9. The device of claim 1, wherein said channel has a substantially V-shaped cross-section and wherein said projection has a substantially V-shaped cross-section.

10. The device of claim 9, wherein said channel and/or said projection have walls, and wherein said walls of said channel and/or said projection slope towards one another at an angle in the range of from 45 degrees to 60 degrees.

11. The device of claim 1, wherein said channel has a substantially square or rectangular cross-section and wherein said projection has a substantially square or rectangular cross-section.

12. The device of claim 1, wherein at least one locking mechanism is provided on said sheath assembly as part of an external manipulation unit of said implant deployment device at the proximal end of the sheath; and wherein at least one locking mechanism is provided on said sheath assembly at a distal end of said implant deployment device.

13. The device of claim 1, including an implant mounted on said implant support element.

14. The device of claim 1, wherein the projection does not reach the base of the channel.

15. The device of claim 1, wherein the implant support element has a bore running longitudinally therethrough and therefore functions as a catheter at least at the location of the locking mechanism.

16. The device of claim 1, wherein said dilator tip has an inner surface that is circular in cross section at the location of the locking mechanism.

17. An implant deployment device including:
an implant support element onto which an implant may be mounted prior to deployment;
a dilator tip distal of an implant;
a sheath assembly including a sheath operable to cover an implant mounted on said implant support element and to cover at least part of said dilator tip until deployment, said sheath being retractable relative to said implant support element, wherein said sheath has an inner surface and said dilator tip has an outer surface and an inner surface, wherein said inner surface of said sheath faces said outer surface of said dilator tip; and
a locking mechanism for preventing relative rotation between the implant support element and the sheath assembly at a distal end thereof, said locking mechanism including at least one co-operating channel and projection;
the projection, being provided on said inner surface of said sheath assembly at or near a distal end thereof and the channel being provided on said outer surface of said dilator tip at or near a distal end thereof;
wherein said implant support element has a diameter, and wherein said channel has a depth in the range of 10 to 20 percent of said diameter of said implant support element, said channel and said projection having substantially a same shape in transverse cross-section, for preventing relative rotation of said sheath and implant support element at said distal end as said sheath is retracted;
said inner surface of said dilator tip having a circular cross section at the location of the locking arrangement; and
said inner surface of said sheath and said outer surface of said dilator tip having a generally round transverse cross-section at the location of the locking arrangement, wherein said generally round transverse cross-section is 80 to 90 percent circular, such that said device has flexibility that is even in different radial directions at least at the location of the locking mechanism.

18. An implant deployment device including:
an implant support element onto which an implant may be mounted prior to deployment;
a dilator tip distal of an implant;
a sheath assembly including a sheath operable to cover an implant mounted on said implant support element and operable to cover at least part of said dilator tip, said sheath being retractable relative to said implant support element, wherein said sheath has an inner surface and said dilator tip has an outer surface and an inner surface, wherein said inner surface of said sheath faces said outer surface of said dilator tip;
a locking mechanism for preventing relative rotation between the implant support element and the sheath assembly at a distal end thereof, said locking mechanism comprising at least one co-operating channel and projection, said locking mechanism being provided on said inner surface of said sheath assembly and on said outer surface of said dilator tip at or near a distal end thereof; and
said inner surface of said dilator tip element has a circular cross section at the location of the locking mechanism; and
each of said inner surface of the sheath and outer surface of the dilator tip have a generally round transverse cross-section at the location of the locking mechanism.

19. The device of claim 18 wherein said generally round transverse cross-section includes a circumference that is at least 70 percent circular.

* * * * *